(12) United States Patent
Howard et al.

(10) Patent No.: US 7,605,924 B2
(45) Date of Patent: Oct. 20, 2009

(54) LASER-ULTRASOUND INSPECTION USING INFRARED THERMOGRAPHY

(75) Inventors: Donald Robert Howard, Troy, NY (US); Harry Israel Ringermacher, Delanson, NY (US); Marc Dubois, Keller, TX (US); Timothy Gerard Richter, Wynantskill, NY (US); Thomas E. Drake, Fort Worth, TX (US)

(73) Assignee: Lockheed Martin Corporation, Bethesda, MD (US)

( * ) Notice: Subject to any disclaimer, the term of this patent is extended or adjusted under 35 U.S.C. 154(b) by 0 days.

(21) Appl. No.: 11/567,405

(22) Filed: Dec. 6, 2006

(65) Prior Publication Data
US 2008/0137105 A1 Jun. 12, 2008

(51) Int. Cl.
*G01B 11/00* (2006.01)
(52) U.S. Cl. .................................. 356/502; 356/432
(58) Field of Classification Search .................. 356/72, 356/432, 502; 73/657; 374/130, 131
See application file for complete search history.

(56) References Cited
U.S. PATENT DOCUMENTS

| | | | | |
|---|---|---|---|---|
| 4,896,278 A | * | 1/1990 | Grove | .......................... 702/36 |
| 6,122,060 A | * | 9/2000 | Drake, Jr. | .................... 356/502 |
| 6,516,084 B2 | * | 2/2003 | Shepard | ...................... 382/141 |
| 6,684,701 B2 | * | 2/2004 | Dubois et al. | .................. 73/579 |
| 6,712,502 B2 | * | 3/2004 | Zalameda et al. | ........... 374/130 |
| 7,095,505 B1 | * | 8/2006 | Beard et al. | .................. 356/502 |
| 2004/0154402 A1 | * | 8/2004 | Drake, Jr. | ..................... 73/621 |

* cited by examiner

*Primary Examiner*—Samuel A Turner
(74) *Attorney, Agent, or Firm*—Bracewell & Giuliani LLP (57) ABSTRACT

An inspection system is provided to examine internal structures of a target material. This inspection system combines an ultrasonic inspection system and a thermographic inspection system. The thermographic inspection system is attached to ultrasonic inspection and modified to enable thermographic inspection of target materials at distances compatible with laser ultrasonic inspection. Quantitative information is obtained using depth infrared (IR) imaging on the target material. The IR imaging and laser-ultrasound results are combined and projected on a 3D projection of complex shape composites. The thermographic results complement the laser-ultrasound results and yield information about the target material's internal structure that is more complete and more reliable, especially when the target materials are thin composite parts.

17 Claims, 8 Drawing Sheets

LASER-ULTRASOUND INSPECTION USING INFRARED THERMOGRAPHY

TECHNICAL FIELD OF THE INVENTION

The present invention relates non destructive testing, and more particularly, to the use of thermal imaging and ultrasonic testing to inspect the internal structures of materials.

BACKGROUND OF THE INVENTION

In recent years, the use of advanced composite structures has experienced tremendous growth in the aerospace, automotive, and many other commercial industries. While composite materials offer significant improvements in performance, they require strict quality control procedures in both the manufacturing processes and after the materials are in service in finished products. Specifically, non-destructive evaluation (NDE) methods must assess the structural integrity of composite materials. Proper assessment demands the ability to detect inclusions, delaminations and porosities both at the near surface region and deep internal region.

Various methods and apparatuses have been proposed to assess the structural integrity of composite structures. One solution uses an ultrasonic source to generate ultrasonic surface displacements in target materials. The ultrasonic surface displacements are then measured and analyzed. The source of the ultrasound may be a pulsed generation laser beam directed at the target. Laser light from a separate detection laser is scattered by ultrasonic surface displacements at the work piece. Then collection optics collect the scattered laser energy. The collection optics are coupled to an interferometer or other device, and data about the structural integrity of the composite structure can be obtained through analysis of the scattered laser energy. Laser ultrasound has been shown to be very effective for the inspection of parts during the manufacturing process.

Typically, a laser source produces sound by thermal expansion at a localized spot on the surface while a probe laser beam, coupled to an interferometer, detects surface displacements or velocity. The thermal expansion due to the absorption of the generation laser produces a displacement that is demodulated by the laser-ultrasound detection system resulting in a pulse at the beginning of the laser-ultrasound signal. This echo is commonly called surface echo. The surface echo may mask any echo produced by a defect near the sample surface. The duration of the surface echo depends on the generation laser pulse duration and on the frequency bandwidth of the detection system. Typically, with a $CO_2$ generation laser and a confocal Fabry-Perot for detection, the surface echo might last up to a few microseconds. Thus any defect that would produce an echo during that time might be masked. For this reason, Laser-ultrasound inspection is sensitive to deep internal defects and less sensitive to near-surface defect.

Transient infrared (IR) thermography, another NDE method, does not efficiently allow for the inspection of polymer-matrix composites due to its insensitivity to defects deeper than a few mm's in polymer-matrix parts.

SUMMARY OF THE INVENTION

Embodiments of the present invention are directed to systems and methods that substantially address the above identified needs and other needs as well. The embodiments of the present invention are further described in the following description and claims. Advantages and features of embodiments of the present invention may become apparent from the description, accompanying drawings and claims.

Embodiments of the present invention combine laser ultrasound and thermal imaging techniques to substantially address the above identified needs and other needs as well. Laser-ultrasound generation techniques may be used to provide a transient heat source. Thus, transient infrared (IR) thermography may be combined with laser ultrasound to provide a more complete non-destructive inspection of polymer-matrix parts (i.e. composite materials).

One embodiment provides an inspection system to examine near surface and deep internal structures of target material. This inspection system combines an ultrasonic inspection system and a thermographic inspection system. The thermographic inspection system is attached to ultrasonic inspection and modified to enable thermographic inspection of target materials at distances compatible with laser ultrasonic inspection. Quantitative information is obtained using depth infrared (IR) imaging on the target material. The IR imaging and laser-ultrasound results are combined and projected on a 3D projection of complex shape composites. The thermographic results complement the laser-ultrasound results and yield information about the target material's internal structure that is more complete and more reliable, especially when the target materials are thin composite parts.

Another embodiment provides a method of inspecting the internal structures of a target. This method involves inducing both ultrasonic displacements and thermal transients at the target material. These ultrasonic displacements may be produced and analyzed using a laser ultrasound system. The thermal transients may be produced using flash lamps and analyzed using a thermographic inspection system. Analysis may involve correlation of both ultrasonic information and thermal information to yield a more complete understanding about the structure of the target. Analyzing ultrasonic displacements for example may yield information about deep internal structures within the composite material. Thermal imagery may yield information about near surface internal structures of the composite material. Correlating the ultrasonic information and thermal information results in a better understanding of the overall internal structure of the target.

Yet another embodiment provides a composite material inspection system. This composite material inspection system This inspection system combines an ultrasonic inspection system and a thermographic inspection system. An ultrasonic detection system is provided to detect the ultrasonic surface displacements at the composite material. A thermal imaging system is provided to detect thermal transients at the composite material. The control module may match thermal imaging acquisition to laser ultrasound acquisition information to aid in the correlation of laser ultrasound information and thermal imagery in order to yield information about the overall internal structure of the target.

BRIEF DESCRIPTION OF THE DRAWINGS

For a more complete understanding of the present invention and the advantages thereof, reference is now made to the following description taken in conjunction with the accompanying drawings in which like reference numerals indicate like features and wherein.

DETAILED DESCRIPTION OF THE INVENTION

Preferred embodiments of the present invention are illustrated in the FIGURES, like numerals being used to refer to like and corresponding parts of the various drawings.

Embodiments of the present invention combine laser ultrasound and thermal imaging techniques to provide a more complete non-destructive inspection of target materials such as but not limited to polymer-matrix parts (i.e. composite materials). One embodiment provides an inspection system operable to examine internal structures of the target material. One embodiment provides an inspection system to examine near surface and deep internal structures of target material. This inspection system combines an ultrasonic inspection system and a thermographic inspection system. The thermographic inspection system is attached to ultrasonic inspection and modified to enable thermographic inspection of target materials at distances compatible with laser ultrasonic inspection. Quantitative information is obtained using depth infrared (IR) imaging on the target material. The IR imaging and laser-ultrasound results are combined and projected on a 3D projection of complex shape composites. The thermographic results complement the laser-ultrasound results and yield information about the target material's internal structure that is more complete and more reliable, especially when the target materials are thin composite parts. Embodiments of the present invention provide for faster inspection rates, improved system reliability, and lower operation costs.

Figure 1:
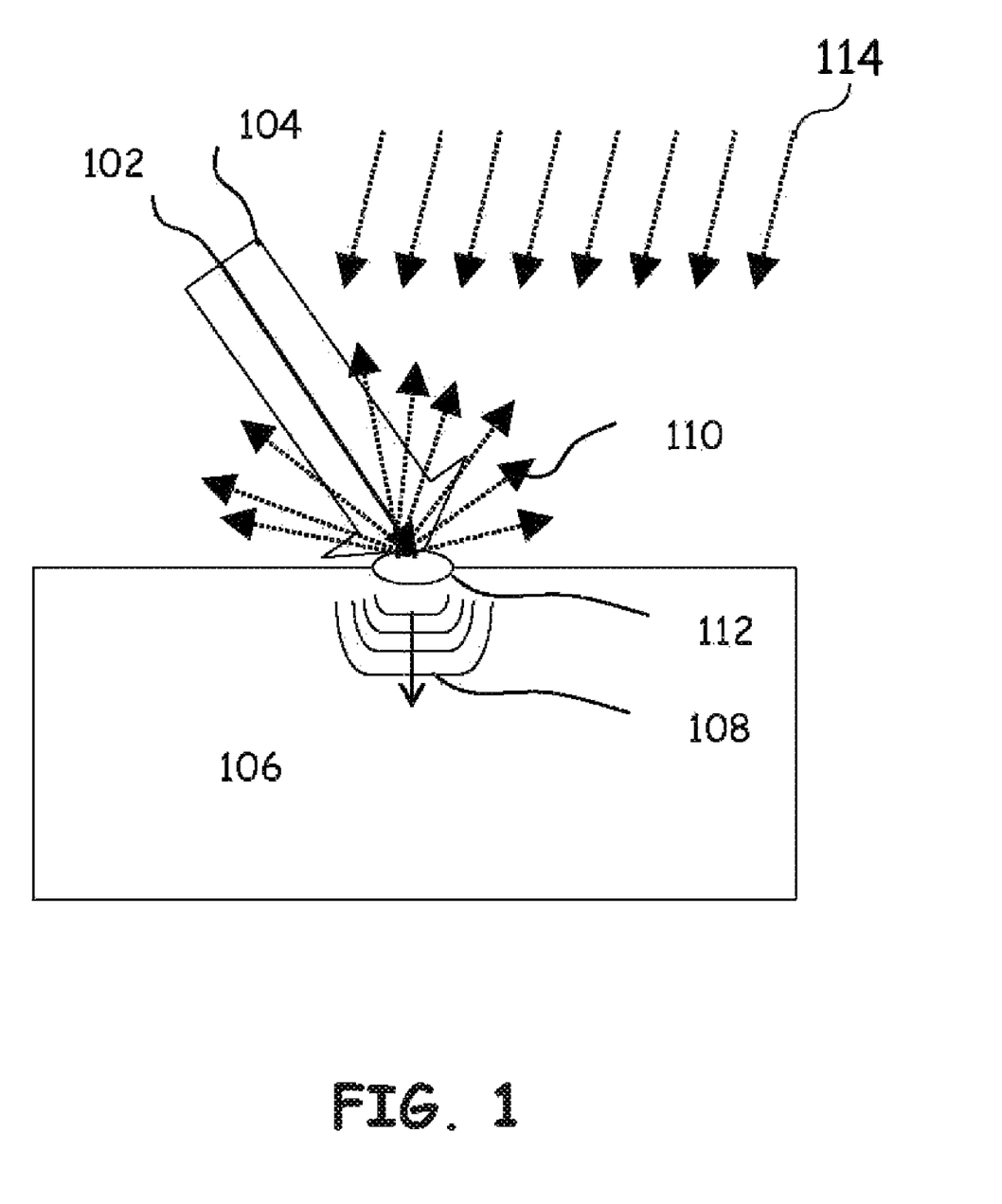
FIG. 1 illustrates the use of generation laser beam and a detection laser beam to generate and detect laser ultrasonic displacements and thermal transients in accordance with embodiments of the present invention.

FIG. 1 illustrates the use of generation laser beam and a detection laser beam to generate and detect laser ultrasonic displacements and thermal transients in accordance with embodiments of the present invention. Laser beam 102 generates ultrasound while illumination (detection) laser beam 104 detects the ultrasound at a target 106, such as a composite material under test. A thermal source, such as flash lamps (not shown) may be used to direct radiation 114, such as infrared (IR), to induce thermal transients in target 106. Thermal radiation may simultaneously illuminate all of target 106. As such there may be a cool down time between thermal imaging and ultrasound inspection. The lasers that relate to the ultrasonic inspection may be coaxially applied to target 106. Generation laser beam 102 causes thermo-elastic expansion 112 in target 106 that results in the formation of ultrasonic deformations or waves 108. Deformations or ultrasonic waves 108 propagate in target 106 and modulate, scatter and reflect detection laser beam 104 to produce phase-modulated light 110 directed away from target 106 which is collected and processed to obtain information describing the internal structure of target 106.

Figure 2:
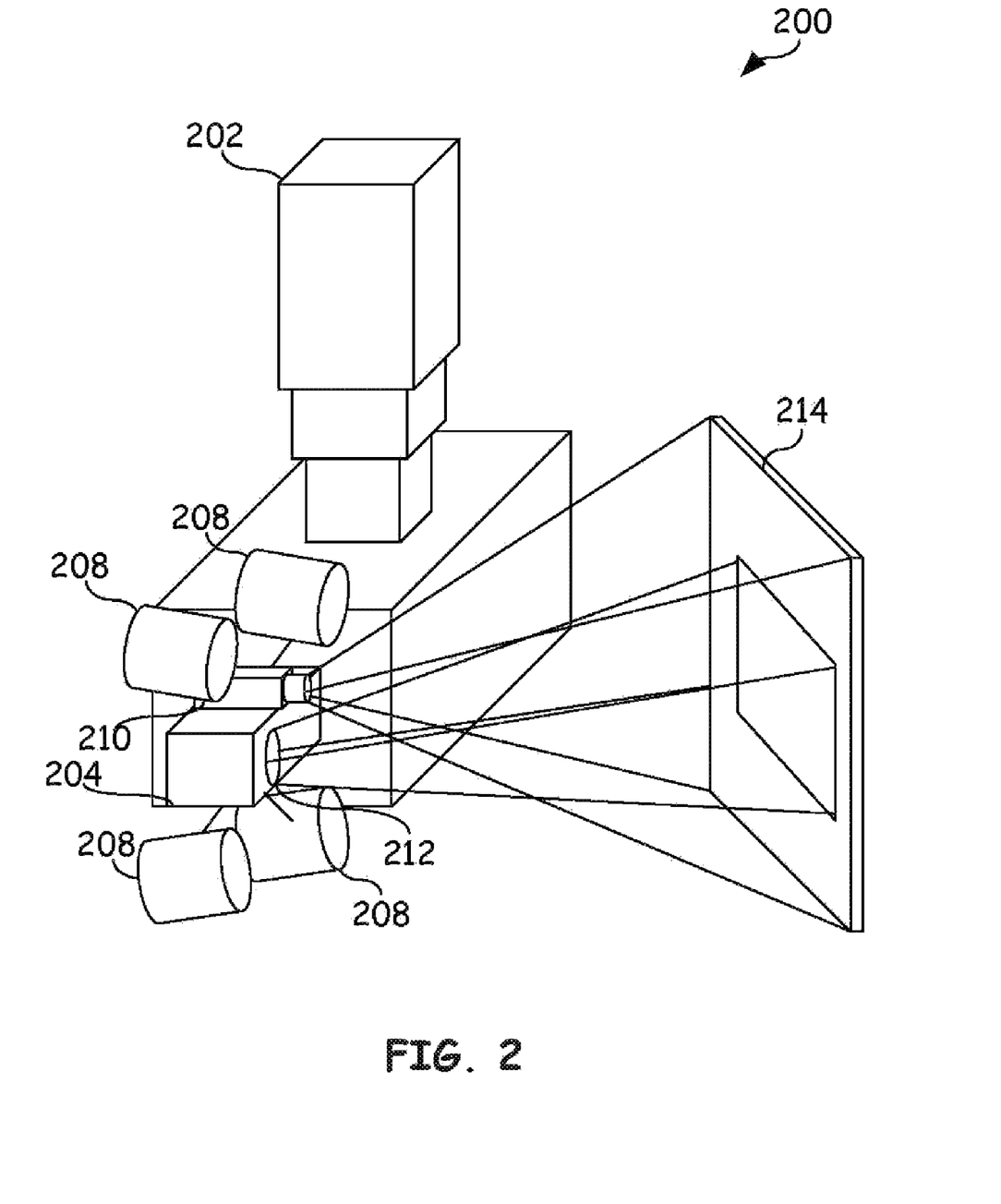
FIG. 2 provides a block diagram to show the basic components of laser ultrasound/thermal imaging system.

FIG. 2 provides a perspective diagram of an inspection system that performs both ultrasonic testing and infrared (IR) thermography in accordance with embodiments in the present invention. Inspection System 200 includes an ultrasonic inspection system coupled to a thermographic inspection system. The ultrasonic inspection system includes a laser ultrasound positioning system 202, and a laser ultrasound head 204 that includes scanning optics. Operation of these will be discussed in further detail with reference to FIG. 3.

The thermographic inspection system includes IR lamps 208 and an IR camera 210. The IR lamps induce thermal transients within composite or target material 214. IR camera 210 is operable to capture the thermal images of target 214. As shown in this embodiment the field of view of camera 210 may be large enough to capture an image of target 214 in a single frame. Alternatively IR camera 210 may capture multiple frames used to create a composite thermal image. A time series of images may be used to create a composite image based on the thermal properties of target 214. This may include for example the determination of a quantitative thermal wall thickness wherein unexpected changes in the quantitative thermal wall thickness indicate discontinuities, potential discontinuities or flaws within target 214.

Figure 3:
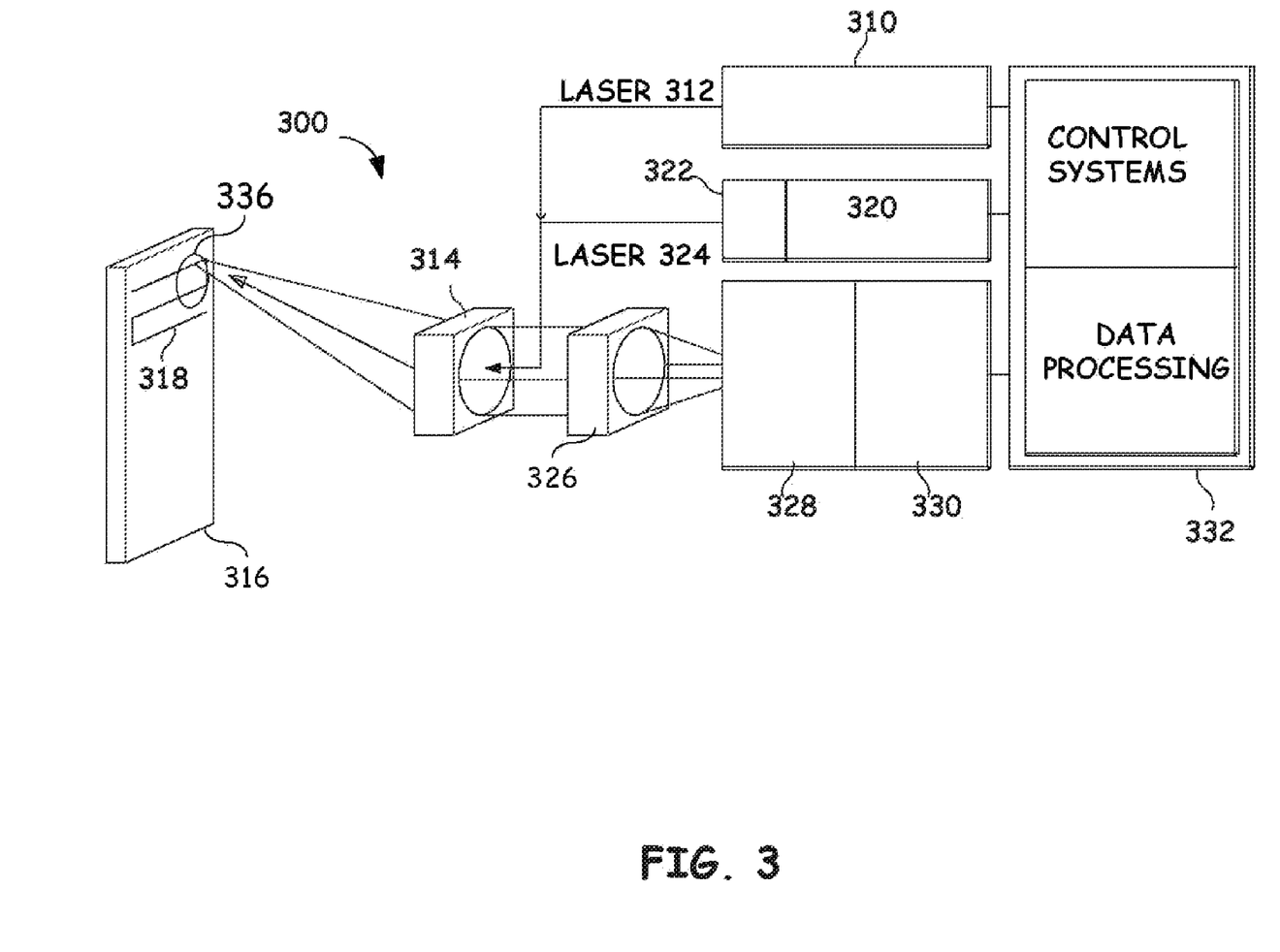
FIG. 3 provides a functional diagram of a laser ultrasound and IR imaging system in accordance with embodiments of the present invention.

FIG. 3 provides a block diagram with the basic components for performing ultrasonic laser testing. Laser ultrasonic inspection system 300 includes generation laser 310, detection laser 320, optical assembly 314, collection optics 326, optical processor 328 and interferometer 330, and control and data processing modules 332. Generation laser 310 produces generation laser beam 312 which optical assembly 314 directs to target 316. As shown, optical assembly 314 includes a scanner or other like mechanism that moves laser beam 312 along a scan or test plan 318. Optical assembly 314 may include visual cameras, depth cameras, IR cameras, range detectors, narrowband cameras or other like optical sensors known to those having skill in the art. These optical sensors each may require calibrations prior to performing an inspection. This calibration verifies the ability of the system to integrate information gathered by various sensors. Generation laser 310 produces an ultrasonic wave 108 and a thermal transient within target 316.

Ultrasonic wave 108 and thermal transient is the result of thermo-elastic expansion 112 of the composite material as the composite material absorbs the generation laser beam. Composite material 316 readily absorbs generation laser beam 312 without ablating or breaking down. Higher powered generation lasers are not necessarily preferred to overcome signal-to-noise ratio (SNR) issues as these can result in ablation of material at the surface of the workpiece, potentially damaging the component. In other embodiments, depending on the material being tested, some ablation may be acceptable in order to increase the SNR of the detected signal. Generation laser beam 312 has appropriate pulse duration, power, and frequency to induce ultrasonic surface deformations and appropriate thermal transients. For example, a transverse-excited atmospheric (TEA) $CO_2$ laser can produce a 10.6 micron wavelength beam for a 100 nanosecond pulse width. The power of the laser must be sufficient to deliver, for example, a 0.25 joule pulse to the target, which may require a 100 watt laser operating at a 400 Hz pulse repetition rate. Generation laser beam 312 is absorbed as heat into the target surface thereby causing thermo-elastic expansion without ablation.

Detection laser 320 operating in pulsed mode or CW mode does not induce ultrasonic displacements. For example, an Nd:YAG laser can be used. The power of this laser must be sufficient to deliver, for example, a 100 milli-joule, 100 micro-second pulse, which may require a one kilo-watt (KW) laser. Detection laser 320 generates detection laser beam 322. Detection laser 320 includes or optically couples to filtering mechanism 324 to remove noise from detection laser beam 320. Optical assembly 314 directs detection laser beam 320 to the surface of composite material 316 which scatters and/or reflects detection laser beam 320. Resultant phase modulated light is collected by collection optics 326. As shown here, scattered and/or reflected detection laser light travels back though optical assembly 314. Optional optical processor 328 and interferometer 330 process the phase modulated light to produce a signal containing information representative of the ultrasonic displacements at the surface of composite material 316.

Figure 4:
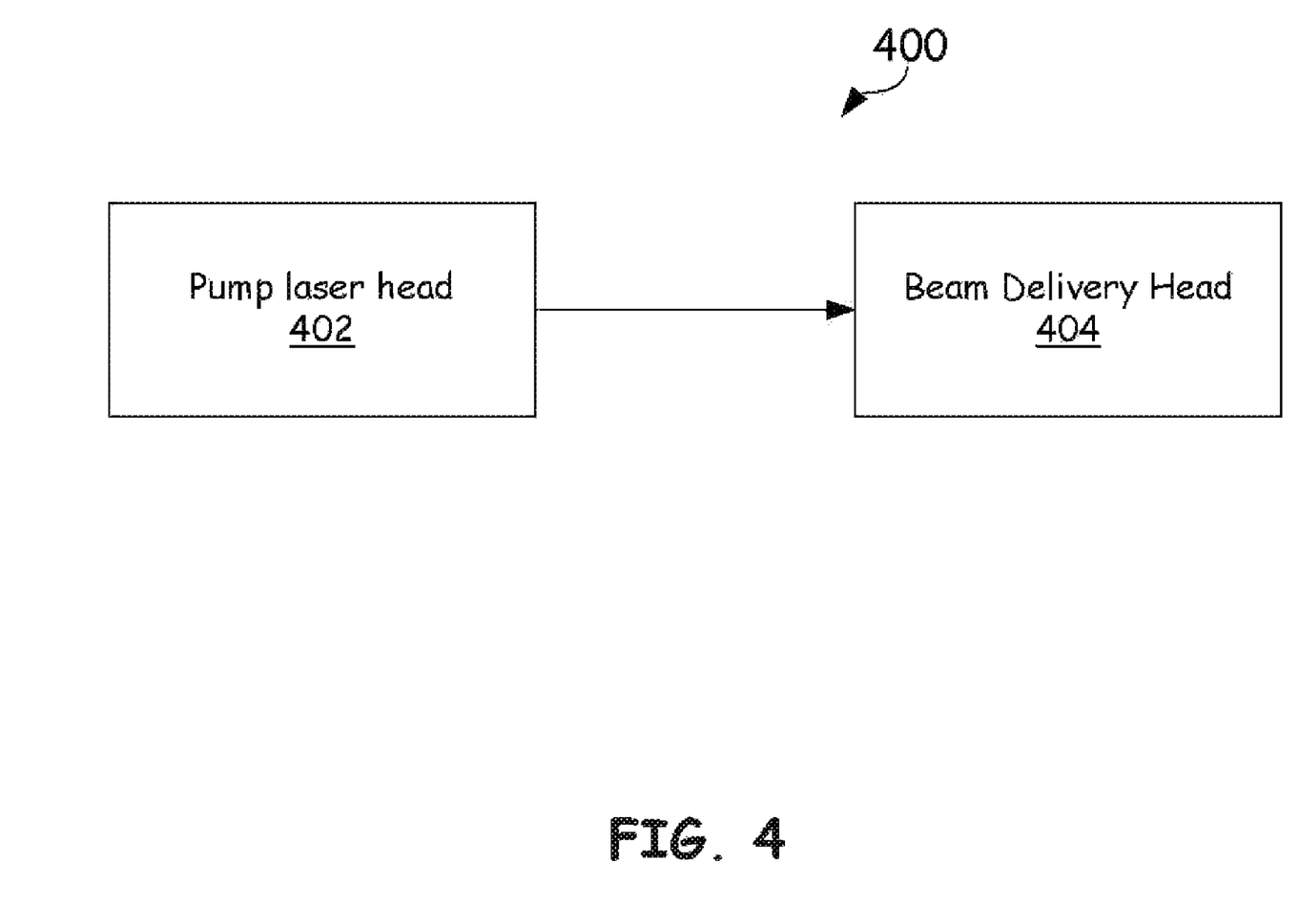
FIG. 4 depicts a block diagram of a generation laser operable to generate ultrasonic displacements and thermal transients in accordance with embodiments of the present invention.

The generation laser beam may be a mid-IR ultrasound generation laser. Such a generation laser provides a compact, high-average power mid-IR laser for ultrasound and thermal transient generation. As shown in FIG. 4, the generation laser 700 includes a pump laser head 402, having a fiber laser therein, fiber coupled to a generation laser head 404. Using fiber lasers allows the laser pump to be located remotely from generation laser head 404. The pump laser head may be coupled via optical fiber 402 to the generation laser head 404.

Locating the pump laser head 402 meters away from generation laser beam delivery head 404 allows a compact mid-IR generation laser head that reduces the overall payload and the stability requirements for robotic or positioning systems used to deliver the generation laser beam and acquire thermal images. Only a compact and light-weight module containing the generation laser beam delivery head and an IR camera is required to be mounted within the inspection head of the robotic system. This allows the deployment of a mid-IR laser source using smaller robots. Thus, new composite inspection opportunities are created for in-field composite NDE using portable laser ultrasound systems and IR thermography systems. These approaches are discussed in U.S. patent application Ser. No. 11/458,377 entitled FIBER LASER FOR ULTRASONIC TESTING which is hereby incorporated for all purposes.

Figure 5:
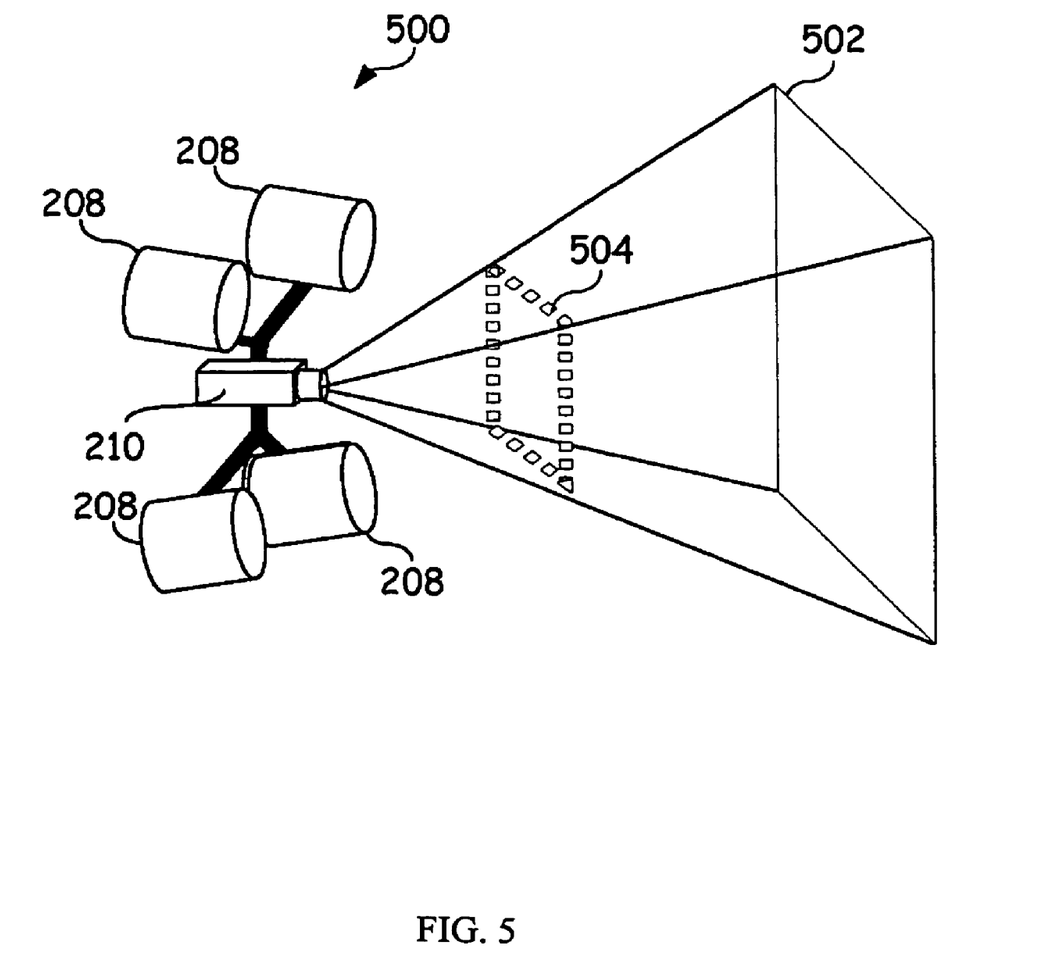
FIG. 5 provides a functional diagram of thermographic inspection system in accordance with embodiments of the present invention.

FIG. 5 provides a functional block diagram of thermographic inspection system. Thermographic inspection system 500 includes thermal imaging cameras (i.e. IR camera 210) and IR flash lamps 208 to induce thermal transients within the target. Flash lamps 208 may have reflectors operable to direct the thermal radiation to a desired location. For example, these reflectors may allow thermal excitation at a larger distance than typically used for thermography. For example, these reflectors allow the flash lamps to be located at a 6 foot standoff instead of the more conventional standoff of 1 foot for thermographic inspection. This allows both the thermographic inspection system 500 and the laser ultrasonic inspection system 300 to be mounted on the same positioning system. This also allows camera 210 to have a larger field of view 502 when compared to field of view 504 associated with a typical standoff distance. Thermographic inspection system 500 captures and analyzes thermal images of the target. These images are processed to yield information about near surface internal structures of target 316.

Data processing and control system 332 coordinates operation of the laser ultrasound system components and thermal imagery components to yield information about internal structures of the target. Data processing and control system 332 directs the operation of both the laser ultrasonic inspection system 300 and the thermographic inspection system 400. The processing and control system analyzes detected ultrasonic displacements and thermal imagery to yield information about the internal structure of the target. The ultrasonic inspection results and the thermographic inspection results can then be combined to provide a more accurate representation of the internal structure of the target wherein this information may be mapped to a computer model of the target. The processing and control system may also direct the sequence of the inspections such that in one embodiment the thermographic inspection may be performed first and then a predetermined amount of time may elapse between the thermographic inspection and the ultrasonic inspection to allow the thermal transient to subside.

Data processing and control system 332 may be a single processing device or a plurality of processing devices. Such a processing device may be a microprocessor, micro-controller, digital signal processor, microcomputer, central processing unit, field programmable gate array, programmable logic device, state machine, logic circuitry, analog circuitry, digital circuitry, and/or any device that manipulates signals (analog and/or digital) based on operational instructions stored in memory. The memory may be a single memory device or a plurality of memory devices. Such a memory device may be a read-only memory, random access memory, volatile memory, non-volatile memory, static memory, dynamic memory, flash memory, cache memory, and/or any device that stores digital information. The memory stores, and data processing and control system 332 executes, operational instructions corresponding to at least some of the steps and/or functions as will be illustrated.

Figure 6:
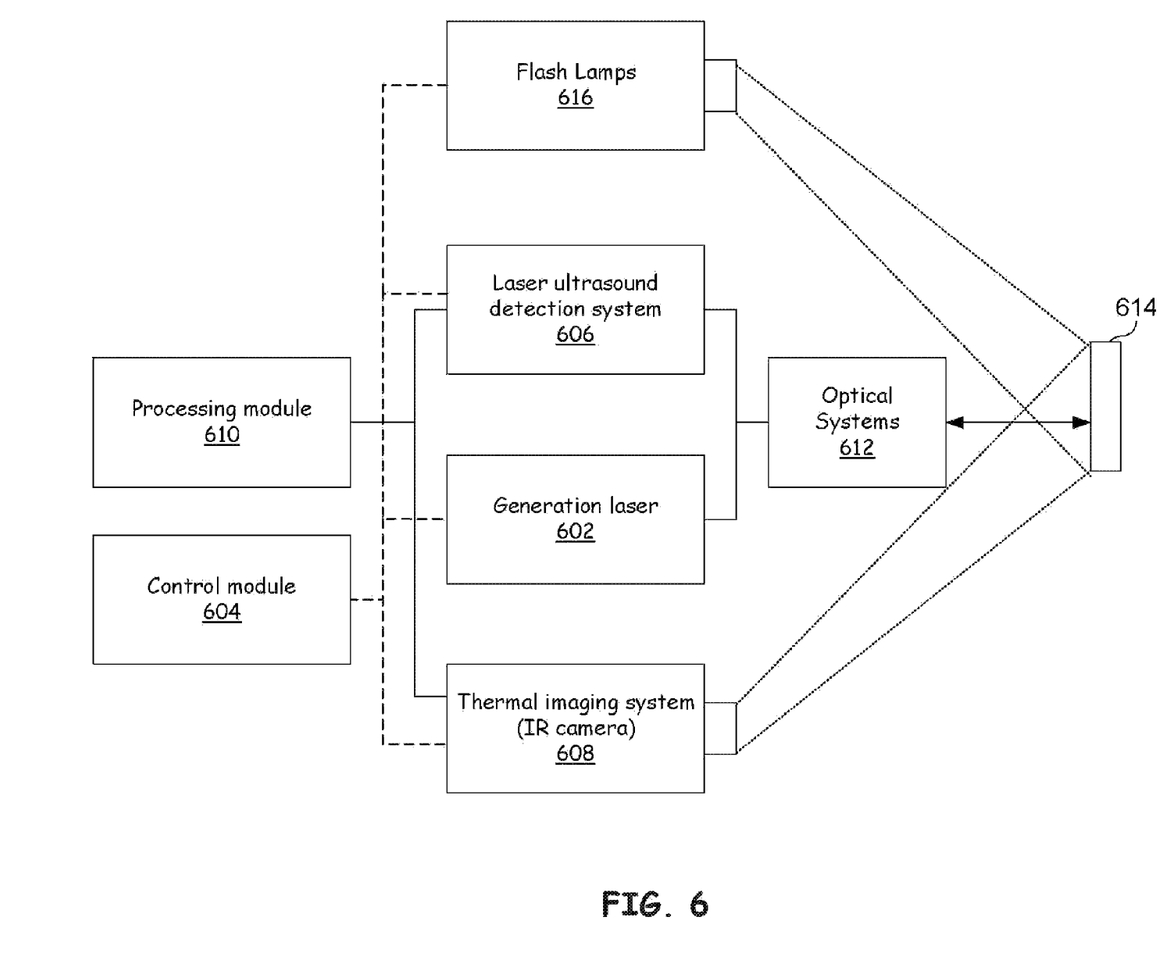
FIG. 6 provides a block or functional diagram of a laser ultrasound and IR imaging system in accordance with embodiments of the present invention.

FIG. 6 provides a block or functional diagram of a laser ultrasound and IR imaging system 600 in accordance with embodiments of the present invention. Laser ultrasound and IR imaging system 600 includes a generation laser 602, a control module 604, a laser ultrasound detection system 606, a thermal imaging system 608, a processing module 610, optical system 612, and flash lamps 616. Generation laser 602 produces a generation laser beam which is directed by optical systems 612 to a target 614 made of materials such as but not limited to composite materials wherein ultrasonic displacements are induced as discussed above. Laser ultrasound detection system 606 generates a detection laser beam which is directed by optical systems 612 to target 614 wherein ultrasonic displacements at the surface of target 614 cause the detection laser beam to be phase-modulated. Optical systems 612 also collect detection laser beam light scattered by the target surface. The laser ultrasound detection system 606 processes the collected phase modulated light in order to develop a signal containing information about the ultrasonic displacements. This signal is provided to processing module 610.

Flash lamps 616 create a thermal transient for thermographic measurements of target 614. A thermal imaging system such an IR camera 608 acquires thermal images or frames of the thermal transients within target 614. The field of view may allow a single frame image of the surface or target 614. Alternatively multiple frames may be acquired to make a composite thermal image. Additional images may be acquired at predetermined times during the thermal transient. These different images are processed to produce a thermographic inspection of the complete area inspected by laser-ultrasound.

The thermographic results complement the laser-ultrasound results and provide in this manner a more complete and more reliable inspection. Transient IR thermography does not by itself provide for the efficient inspection of composite parts such as polymer matrix composites. Transient IR thermography is sensitive only to the top surface of the composite parts because of the low thermal conductivity of the polymer matrix. Thus, IR thermography cannot be used to identify to detect and identify deep defects within a polymer matrix or composite part.

Laser ultrasound and IR imaging system 600 incorporates both laser ultrasound which provides a deep internal inspection system and thermal imaging to address near surface inspection of target 614. This addresses problems associated with the fact that laser ultrasound inspection may be less sensitive to near surface defects. By combining these two techniques a more complete non-destructive inspection of a composite part or material is possible than was possible when only using laser ultrasound or IR thermography.

Figure 7:
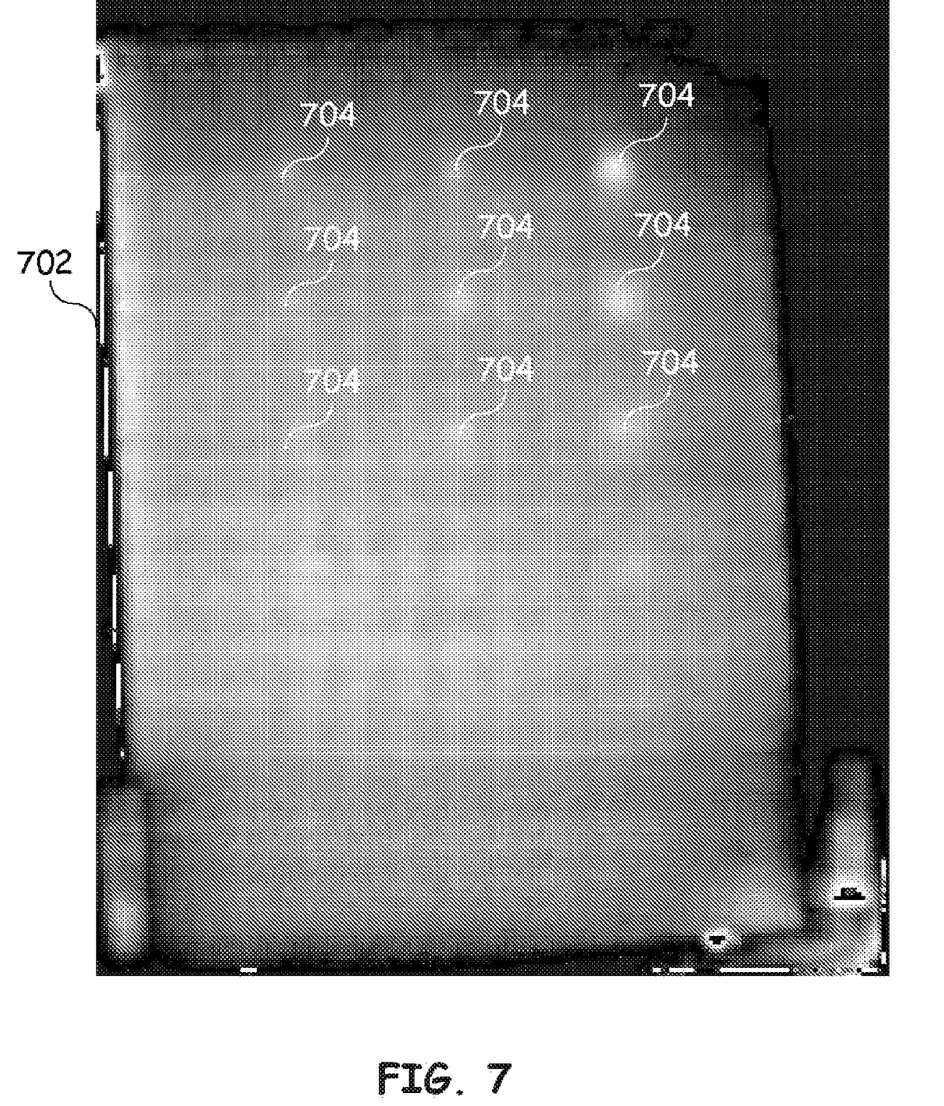
FIG. 7 shows the infrared results obtained by analyzing thermal transients within a polymer plate with flat-bottom holes in accordance with embodiments of the present invention.

FIG. 7 shows the infrared results obtained by analyzing thermal transients within a polymer plate with flat-bottom holes in accordance with embodiments of the present invention. A series of thermal image may be gathered at predetermined times during the thermal transient initiated by the firing of the flash lamps. Each point on the surface of the target experiences a unique thermal transient. These thermal transients may be used to determine the thermal properties associated with the target material. For example a quantitative thermal wall thickness may be determined by analyzing thermal imagery over time at the target. This may be presented in the form of a synthetic visual image as is illustrated in FIG. 7. This processing approach analyzes infrared images (more specifically temperature variations as a function of time within the different images are analyzed). A relative temperature variation curve is built from all the IR images for each point of the IR camera.

Another embodiment may provide a scanned IR thermography technique to inspect materials for near surface defects. This allows the peak thermal load of the target to be limited in that only a small portion of the target is heated at any one time. Such a system uses a scanned laser to induce thermal transients.

The defects in the target 702 clearly appear in the gray scale image 700. Image 700 includes various points 704 within material 702. This image may be generated using an imaging method such as that described in U.S. Pat. No. 6,367,969 entitled "Synthetic reference thermal imaging method," which is incorporated by reference for all purposes. IR transient thermography analysis approaches may be used to accurately measure the thickness of a target and provide a visual coded display indicative of its cross-sectional thickness over a desired area of the target.

Basically, IR transient thermography use of an inflection point in a temperature-time (T-t) response analysis of the surface of a rapidly heated target, preferably obtained from "front-side" IR camera observations. This inflection point occurs relatively early in the T-t response and is essentially independent of lateral heat loss mechanisms. (Such considerations may be of particular relevance, for example, when working with metals since, due to the high thermal conductivity of metals, the thermal response of a metal target is fairly quick and, consequently, the time available for obtaining thermal data measurements is usually short). The inflection point is extracted from thermal data acquired over a predetermined time period from successive IR camera image frames. Preferably, this time period is at least somewhat longer than an anticipated characteristic time based on an estimation of the thickness of the target being evaluated.

Thermal reference data is computed for each (x,y) pixel location of the imaged target and then used to determine contrast as a function of time for each pixel. A computer system controls the imaging system, records and analyzes surface temperature data acquired via the IR camera, and provides a color or gray pattern-keyed image that accurately corresponds to thickness of the target. This information may be merged with laser ultrasound data to produce a more detailed internal picture of the target.

The acquisition of surface temperature data is initiated by firing the generation laser to illuminate and heat a portion of the surface of the target. Thermal image frames are then recorded over a period of time after each generation laser pulse and the recorded images used to develop a temperature-time (T-t) history, such as that associated with thermal transients.

Heat flow analysis of the T-t history is then conducted for each pixel in the acquired image frames to determine the thickness of the target at each resolution element location. Conventionally, analysis of transient heat flow through solid portions of a target requires determining a characteristic time required for a "pulse" of thermal energy to penetrate the target at a first surface, reflect off an opposite surface and return to the first surface. Since this characteristic time is related to the distance between the two surfaces, it can be used to determine the thickness of the target between the two surfaces at a desired point. A contrast-versus-time curve is determined for each (x,y) pixel location corresponding to each resolution element of the target surface.

Figure 8:
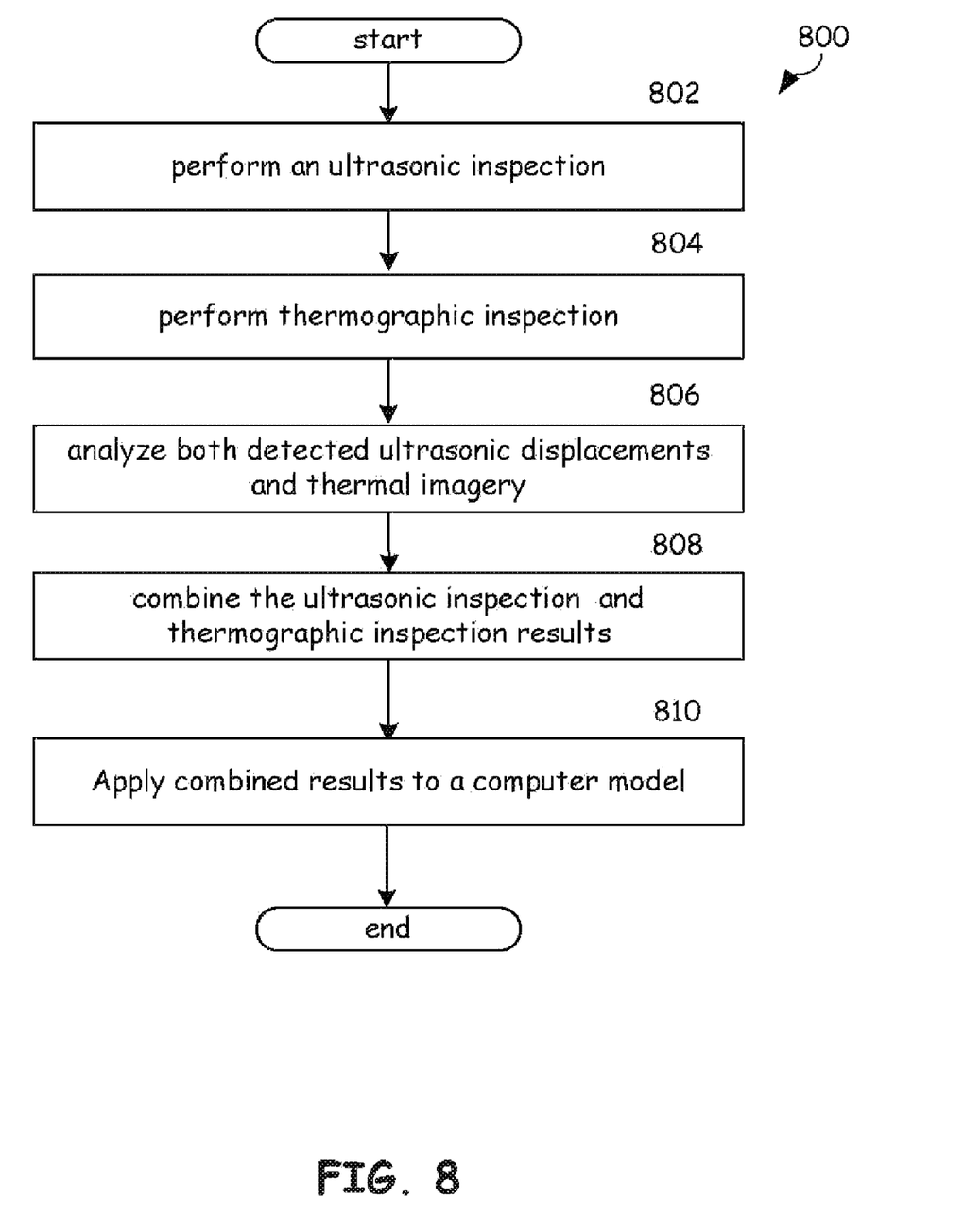
FIG. 8 provides a logic flow diagram that describes a method to inspect target material in accordance with embodiments of the present invention.

FIG. 8 provides a logic flow diagram that describes a method to inspect target materials in accordance with embodiments of the present invention. This method combines ultrasonic inspection and thermographic inspection in order to provide a more accurate and reliable examination of the target materials. Operations 800 begin with step 802. In step 802, a thermographic inspection may be performed. After the thermographic inspection is performed an ultrasonic inspection may be performed. As described previously the ultrasonic inspection system and thermographic inspection system may share a common positioning system in order to aid in the correlation of ultrasonic data and thermographic data. There may be a time interval in-between the thermographic inspection and the ultrasonic inspection of step 804. This allows the target materials to return to thermal equilibrium or for the thermal transient to subside. This time interval prevents the thermal transient from impacting the results of the ultrasonic inspection. In step 806 the detected ultrasonic displacements associated with the ultrasonic inspection and thermal imagery associated with the thermographic inspection is analyzed to produce ultrasonic inspection results and thermographic inspection results. In step 808 these results are combined.

Thermography allows a synthetic image or other representation to be made of the target material. This may involve the determination of a quantitative thermal thickness arrived at by analyzing the thermal imagery. A change in the quantitative thermal wall thickness may indicate a near surface flaw in the target material at the point where the unexpected change in the quantitative thermal wall thickness occurs. This information may be visualized by a contrast display where an abrupt change in contrast indicates a discontinuity or change in the quantitative thermal wall thickness.

Combining these results in a more accurate understanding of the target materials. Thermographic inspection is better suited to examine the target materials for surface defects while ultrasonic inspection is better suited to deeper internal defects. These results may be combined and applied to the computer model in step 810. The combination of the thermographic inspection system and ultrasonic inspection system allows both inspection systems to share a common positioning platform. Furthermore, laser ultrasound positioning may be used to calibrate the positioning of the thermographic inspection system. This allows more accurate analysis and correlation of thermographic and ultrasonic data. Included herein is a method of determining a thickness of the target material wherein only the thermographic inspection of the target materials is performed when the thickness of the target materials is less than a predetermined thickness, and both the thermographic inspection of the target materials and the ultrasonic inspection of the target materials are performed when the thickness of the target materials is greater than the predetermined thickness.

As one of average skill in the art will appreciate, the term "substantially" or "approximately" as may be used herein, provides an industry-accepted tolerance to its corresponding term. Such an industry-accepted tolerance ranges from less than one percent to twenty percent and corresponds to, but is not limited to, component values, integrated circuit process variations, temperature variations, rise and fall times, and/or thermal noise. As one of average skill in the art will further appreciate, the term "operably coupled", as may be used herein, includes direct coupling and indirect coupling via another component, element, circuit, or module where, for indirect coupling, the intervening component, element, circuit, or module does not modify the information of a signal but may adjust its current level, voltage level, and/or power level. As one of average skill in the art will also appreciate, inferred coupling (i.e., where one element is coupled to another element by inference) includes direct and indirect coupling between two elements in the same manner as "operably coupled". As one of average skill in the art will further appreciate, the term "compares favorably", as may be used herein, indicates that a comparison between two or more elements, items, signals, etc., provides a desired relationship. For example, when the desired relationship is that signal 1 has a greater magnitude than signal 2, a favorable comparison may be achieved when the magnitude of signal 1 is greater than that of signal 2 or when the magnitude of signal 2 is less than that of signal 1.

Although the present invention has been described in detail, it should be understood that various changes, substitutions and alterations can be made hereto without departing from the spirit and scope of the invention as defined by the appended claims.

What is claimed is:

1. A method to inspect target materials, the method comprising:
    performing a laser ultrasonic inspection of the target materials using a laser ultrasonic inspection system having a generation laser to induce ultrasonic acoustic vibrations in the target material and having a detection laser to detect the vibrations;
    performing thermographic inspection of the target materials using a thermographic inspection system;
    providing the laser ultrasonic inspection testing system and the thermographic inspection system at a standoff distance from the target typical for a laser ultrasonic inspection system but greater than typically used for thermography; and
    analyzing both laser ultrasonic inspection results and thermographic inspection results to determine an internal structure of the target materials.

2. The method of claim 1, wherein the ultrasonic inspection results and the thermographic inspection results of the target materials are combined onto a model of the target materials.

3. The method of claim 1, further comprising determining quantitative thermal wall thickness, and identifying a flaw within the target material where an unexpected change occurs in the quantitative wall thickness.

4. The method of claim 1, further comprising waiting a predetermined amount of time between performing the thermographic inspection and the ultrasonic inspection, wherein the thermographic inspection of the target materials is performed prior to the ultrasonic inspection of the target materials.

5. The method of claim 1, wherein the thermographic inspection comprises:
    illuminating the target materials to induce a thermal transient in the target materials;
    acquiring thermal imagery of the target materials over time; and
    analyzing the thermal imagery of the target materials to obtain information about the target materials.

6. The method of claim 1, wherein the thermographic inspection system includes a reflective flash lamp and a camera, the method further comprising, illuminating the target materials with the reflective flash lamp at the standoff distance, so the thermographic inspection system and the laser inspection system can be mounted on the same positioning system and the camera can have a larger field of view.

7. The method of claim 1, further comprising:
    analyzing ultrasonic displacements detected in the ultrasonic inspection results so that when the target material comprises a composite material information about a deep internal structure of the composite materials is obtained; and
    analyzing thermal imagery of the target materials from the thermographic inspection results so that when the target material comprises a composite material information about a near surface internal structure of the composite materials is obtained.

8. The method of claim 1, wherein the ultrasonic inspection comprises:
    generating a detection laser beam;
    directing the detection laser beam to the surface of the target materials;
    scattering the detection laser beam at the surface of the target materials to produce light phase-modulated by ultrasonic surface displacements;
    collecting the phase modulated light;
    processing the phase modulated light to obtain data representative of the ultrasonic surface displacements at the surface; and
    collecting the data to analyze the target materials.

9. An inspection system operable to inspect an internal structure of a target comprising:
    a laser ultrasonic inspection system operable to inspect the internal structure of the target by creating and detecting ultrasonic displacements in the target;
    a thermographic inspection system operable to inspect the internal structure of the target and obtain thermal imagery of the target and mounted on the same positioning system as the laser ultrasonic inspection system that is disposed at a standoff distance from the target typical for a laser ultrasonic inspection system but greater than typically used for thermography;
    a processing and control system operable to:
    analyze the thermal imagery of the target to yield thermographic inspection results about the internal structure of the target;
    analyze the detected ultrasonic displacements at the target to yield ultrasonic inspection results about the internal structure of the target; and combine the ultrasonic inspection results and the thermographic inspection results of the target materials to obtain information about the internal structure of the target.

10. The inspection system of claim 9, wherein the laser ultrasonic inspection system comprises:
a detection laser operable to generate a detection laser beam operable to illuminate the ultrasonic surface displacements at the target;
collection optics for collecting light phase-modulated by ultrasonic surface displacements from the detection laser beam scattered by the target surface;
an interferometer to process the phase modulated light and generate at least one output signal; and
an optical processing unit to process the at least one output signal to obtain data representative of the ultrasonic surface displacements at the target.

11. The inspection system of claim 9, wherein the thermographic inspection system comprises an infrared (IR) transient thermography system.

12. The inspection system of claim 11, wherein a generation laser beam is created by the ultrasonic inspection system to induce vibrations in the target, and wherein the IR transient thermography system comprises an IR sensitive camera operable to acquire image frames of the target illuminated by the generation laser beam.

13. The inspection system of claim 12, wherein image frames of the target comprise an array of pixels and are assigned a frame number that corresponds to elapsed time, wherein a quantitative thermal wall thickness is determined by analyzing sequential frames of thermal imagery.

14. The inspection system of claim 12, wherein the processing unit correlates the detected ultrasound displacements and the thermal imagery.

15. The inspection system of claim 9, further comprising a control module operable to match thermal imaging frame acquisition to a pulse rate of a generation laser beam.

16. The inspection system of claim 9, further comprising:
a processing unit so that when the target material comprises composite material, the processing unit: analyzes detected ultrasonic displacements to yield information about a deep internal structure of the composite material;
analyzes thermal imagery at the target to yield information about a near surface internal structure of the composite material; and
correlates information about the deep internal structure of the composite material and the near surface internal structure of the composite material.

17. A large area composite inspection system, comprising:
a generation laser operable to generate a pulsed laser beam operable to induce ultrasonic displacements and thermal transients at a composite material under test;
a laser ultrasonic detection system operable to detect the ultrasonic surface displacements at the composite material;
a thermal imaging system operable to detect the thermal transient at the composite material and mounted with the laser ultrasonic detection system together at a standoff distance from the composite material under test typical for a laser ultrasonic inspection system but greater than typically used for thermography;
a control module operable to match thermal imaging frame acquisition to a pulse rate of the generation laser beam;
a processor operable to:
analyze both detected ultrasonic displacements at the composite material and thermal imagery of the composite material to yield information about the internal structure of the composite material.

* * * * *